United States Patent [19]

Goodfellow et al.

[11] Patent Number: 5,750,506
[45] Date of Patent: May 12, 1998

[54] BRADYKININ ANTAGONISTS WITH EXTENDED HYDROPHOBIC SIDE CHAINS

[75] Inventors: Val S. Goodfellow; Heather B. Kroona, both of Westminster; Eric T. Whalley, Golden; Francine E. Wincott, Longmont; Dana A. Zummach, Westminster, all of Colo.

[73] Assignee: Cortech, Inc., Denver, Colo.

[21] Appl. No.: 647,281

[22] Filed: May 13, 1996

Related U.S. Application Data

[63] Continuation of Ser. No. 077,998, Jun. 18, 1993, abandoned.

[51] Int. Cl.$^6$ ............... A61K 38/08; C07K 7/18
[52] U.S. Cl. ............... 514/15; 514/2; 530/314; 530/328
[58] Field of Search ............... 530/314, 328; 514/15, 2

[56] References Cited

U.S. PATENT DOCUMENTS 4,693,993 9/1987 Stewart et al. ............... 514/14
4,801,613 1/1989 Stewart et al. ............... 514/14
4,923,963 5/1990 Stewart et al. ............... 530/314
5,162,497 11/1992 Coy et al. ............... 530/314
5,416,191 5/1995 Cheronis et al. ............... 530/314

OTHER PUBLICATIONS

Vevek et al. "Succinyl Bis—Bradykinins: Potent Agonists with exceptional resistance to Enzymatic Degradation", J. Proc., 8th Am. Pept. Symp. pp. 381–384, 1983.
Schild, "pA. A New Scale for the Measurement of Drug Antagonism", Brit.j.Pharmacol. (1947).2, 189–206.
Arunlakshana et al. "Some Quantitative Uses of Drug Antagonists", Brit. J. Pharmacol. (1959), 14, 48.
Ronald M. Burch. "Bradykinin Antagonists—Basic and Clinical Research", Nova Pharmaceutical Corp. Baltimore, MD Marcel Dekker, Inc., pp. 52–55, 60–63, 80–83, date is not available.

*Primary Examiner*—Cecilia J. Tsang
*Assistant Examiner*—Anish Gupta
*Attorney, Agent, or Firm*—Cushman Darby & Cushman IP Group of Pillsbury Madison & Sutro LLP

[57] ABSTRACT

Bradykinin antagonists, particularly $Cys^6$ analogs, which have an extended hydrophobic side chain.

24 Claims, No Drawings

BRADYKININ ANTAGONISTS WITH EXTENDED HYDROPHOBIC SIDE CHAINS

This is a continuation of application Ser. No. 08/077,998, filed Jun. 18, 1993, now abandoned.

FIELD OF THE INVENTION

The present invention relates to antagonists of bradykinin receptors. These antagonists are characterized by an extended hydrophobic side chain which has been found to increase antagonist potency. The compounds are useful for the treatment of conditions mediated by bradykinin including sepsis, inflammatory diseases, edema, burns, and airway hypersensitivity. The extended hydrophobic side chains provide extensions or "linkers" which allow the attachment of other bioactive molecules in order to function as therapeutic compounds targeting multiple receptor types or enzymes.

RELATED APPLICATIONS

Ser. No. 07/859,582, filed Mar. 27, 1992 and Ser. No. 08/026,684, filed Jan. 8, 1993, disclose bradykinin antagonists which are joined together by a bridging link. The same or different bradykinin antagonists may be linked together. Modified monomers comprising a single bradykinin antagonist component and a linker are also disclosed. The linkage of a bradykinin antagonist and a non-bradykinin antagonist component is also described.

Ser. No. 07/974,000, filed Nov. 10, 1992 discloses heterodimers which comprise a bradykinin antagonist component linked to a component having a different activity, for example, an elastase inhibitor.

BACKGROUND OF THE INVENTION

Bradykinin (BK) and related kinins are endogenous peptides hormone released by proteolytic cleavage of kininogens by a group of endopeptidases known as kallikreins. Bradykinins are mediators in eliciting many pathophysiological responses including pain and hyperalgesia via stimulation of peripheral A- and C- fiber neurons.[1–7] There is evidence that BK plays an important role in inflammatory response[8–11] and is a significant mediator in several disease states including hypotension associated with sepsis[12] and bronchopulmonary disorders including asthma.[13] There is also compelling evidence that bradykinin antagonists may be useful in the treatment of edema (swelling) in head trauma,[14] edema and pain from severe burns,[15] migraine pain,[16] and pain associated with surgical procedures or cancer.[17]

Representative of the compounds disclosed in Ser. No. 07/859,582 and Ser. No. 08/026,684 is the compound (1) which is structurally illustrated by the following:

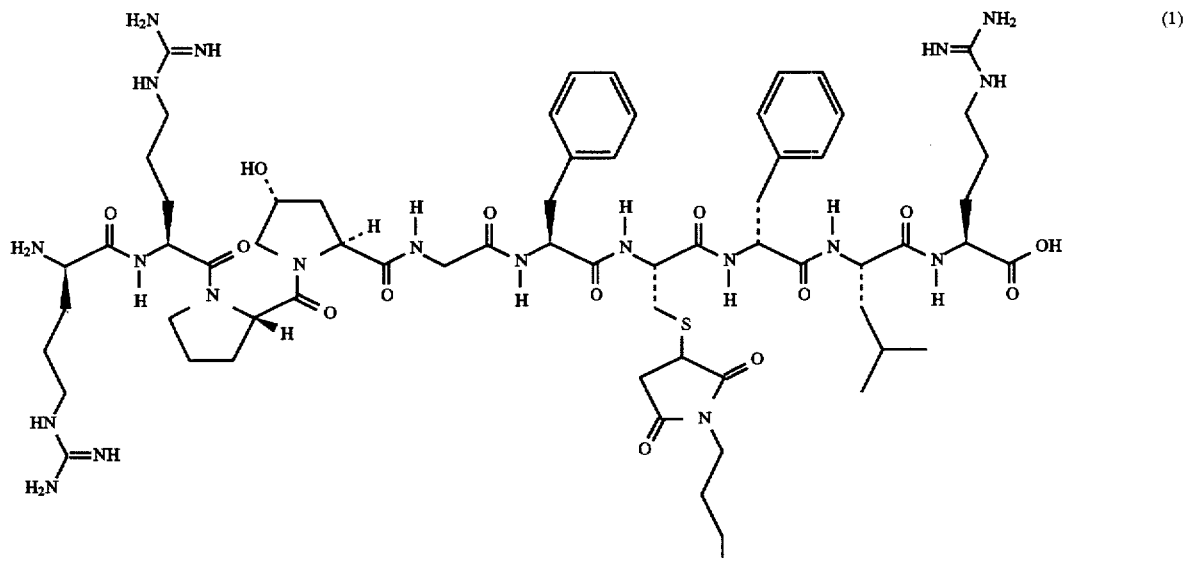

(1)

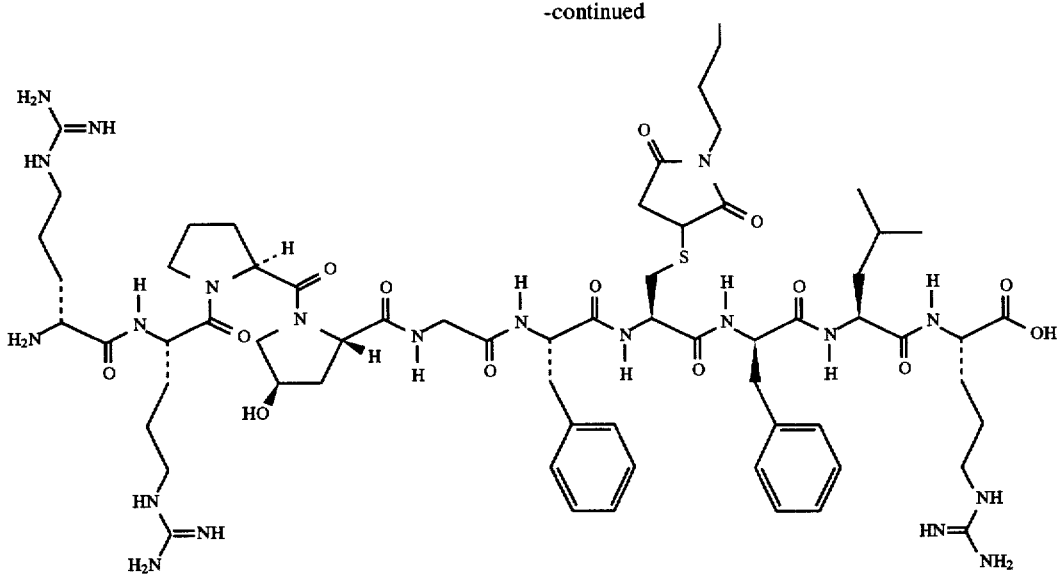

Compound (1) may be more simply illustrated as follows:
D-Arg-Arg-Pro-Hyp-Gly-Phe-NH-C(R)-CO-D-Phe-Leu-Arg
where

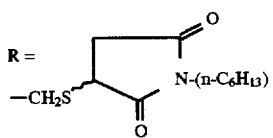

Compound (1) is a bradykinin type 2 ($BK_2$) receptor antagonist which is formed by dimerization of a decapeptide (2):

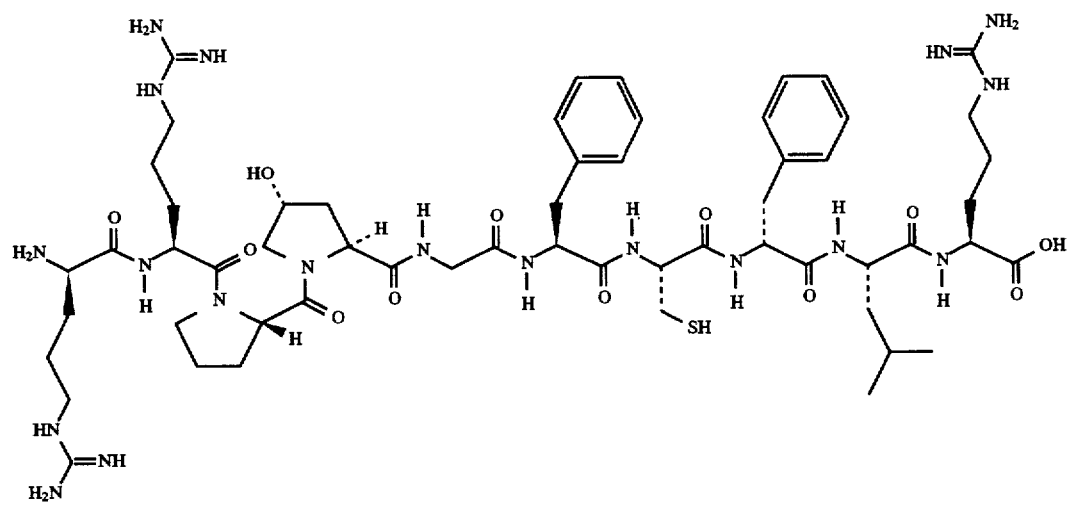

which by itself demonstrates less potent $BK_2$ antagonist activity than dimer (1).

Dimer (1) is formed by linking together two molecules of the decapeptide (2) by means of a bis-maleimido hexane linking group via the sulfhydryl groups of the 6-position cysteine of the decapeptide.

The dimerized structure results in compound (1) with approximately 10 to 100 times the potency of the monomeric precursor (2) in functional tissue assays.[18] Although compound (1) is difficult to detect in human or animal blood following intravenous administration, the compound exhibits long duration of action (5–8 hours) following administration as a bolus dose.[19]

The reasons why compound (1) is so much more effective than (2) is not fully understood. However, one possible explanation for the unexpected potency and duration of action obtained with compound (1) is that the linker moiety may serve to target the molecule to cell membranes where it is then delivered by lateral diffusion to the membrane bound $BK_2$ receptor. Recently, Herbette[20] has reviewed the importance that prior capture of an antagonist by the cell membrane may have for molecules intended to target membrane bound receptors. Such prior capture may play a significant role in in vivo potency, by radically affecting pharmacokinetics and pharmacodynamics of the drug. Alternatively, the enhanced potency and duration of action of (1) in vivo may be the result of enhanced stability to proteolytic degradation and the ability of the antagonist to address specific hydrophobic binding sites on the receptor or proximate membrane surfaces.

While it is possible that each of the foregoing may play a role in explaining the enhanced activity of (1), it appears that other factors may be even more important as far as antagonist potency is concerned. Attachment of a hydrophobic side chain can increase antagonist potency, but such modification must be done at a particular position and with a specific molecular geometry to maximize potency in functional tissue assays. This has been illustrated by synthesizing analogs of (2) and substituting at each amino acid position with a cysteine modified by an S-(N-hexyl)-succinimide moiety. Optimal activity was obtained by substitution at position 6 in the peptide chain. This is in contrast to the general teaching in the art which is that the most potent bradykinin antagonists under investigation as therapeutic agents (HOE-140, NPC 17761, NPC 17731) possess serine residues at the 6 position. Stewart, for example, has reviewed most of the known substitutions at position 6 in bradykinin antagonists and none were shown to greatly enhance potency[21].

SUMMARY OF THE INVENTION

The present invention is based on the finding that a dimeric peptide structure of an (N-alkyl)-succinimide side chain is not necessary to obtain optimum antagonist potency provided that the bradykinin receptor antagonist is modified to include an extended rigid side chain, preferably, but not necessarily, in the 6-position of the peptide. Thus, replacement of the succinimide ring referred to earlier by a variety of rigid structures, has been found to produce very potent antagonists in a non-dimeric structure. According to the invention, a pyrrolidinone side chain is preferred for intrinsic potency. However, more hydrophobic "scaffolds" have been found to give compounds which are essentially irreversible in recovery or "wash out" experiments, and may possess superior pharmacokinetic and pharmacodynamic properties for a particular therapeutic application.

A wide variety of bradykinin receptor antagonists can be modified, according to the invention, to include an extended rigid hydrophobic side chain to provide increased antagonist activity. The nature of the side chain can be widely varied, as discussed hereinafter. The same is true for the positioning of the side chain although the 6-position of the bradykinin antagonist is generally preferred.

DETAILED DESCRIPTION OF THE INVENTION

Broadly defined, the compounds of the invention are bradykinin receptor antagonists of the following structure:

wherein:
X is oxygen, $CH_2O$, sulfur, $CH_2S$ or $CH_2$, and
$AA_1$ is an amino acid residue derived from D-phenylalanine, D-Tic, D-(2-indanyl)-glycine, D-(cyclopentyl)glycine or D-hydroxyproline, or proline substituted at the 3- or 4-position by alkyl or arylalkyl ethers or thioethers;
$AA_2$ is an amino acid residue derived from L-Oic, L-cyclopentylglycine, leucine, phenylalanine or proline or proline substituted at the 3- or 4-position by alkyl or arylalkyl ethers or thioethers;

$AA_3$ is L-arginine or common replacements for arginine as practiced in the art of medicinal chemistry, i.e. pharmaceutically acceptable equivalents of arginine, which produce a positively charged heteroatom at physiological pH such as lysine, or analogs containing alkyl amines, benzamidine, piperidines, alkylguanidines or alkyl phosphonium moieties;
R is hydrogen, acetyl,
  D-Arg-Arg-Pro-Hyp-Gly-$AA_4$,
  D-Arg-Arg-Pro-Pro-Gly-$AA_4$,
or where $AA_4$ is an amino acid residue derived from L-thienylalanine or L-phenylalanine;
n=0 to 20, and D-Arg or Arg can be replaced by glycine analogs containing side chains containing common replacements for arginine as practiced in the art of medicinal chemistry, which produce a positively charged heteroatom at physiological pH such as lysine or analogs containing N-alkylamines, benzamidine, piperidines, alkylguanidines or alkyl phosphonium moieties; and
Z is selected from the group consisting of:

(i)

(ii)

(iii) a prenyl group, where prenyl is defined as a naturally occurring lipid moiety such as prenyl, geranyl, farnesyl, geranylgeranyl.
(iv) alkyl, straight or branched, possessing 1 to 20 carbon atoms, or alkenyl, straight or branched containing 2 to 20 carbon atoms and 1 to 4 double bonds, a hydrocarbon chain of 2 to 20 carbon atoms, either straight or branched and containing 1 to 4 alcohol or ether oxygen atoms, or alkylaryl containing 1 to 4 aromatic rings and 7 to 25 carbon atoms.

(v)

(vi)

or

X is $—(CH_2)_m CONHZ$ or $(CH_2)_m NHCOZ$ where m is 0 to 5 and Z is
(vii) alkyl, straight or branched, possessing 1 to 20 carbon atoms, alkenyl, straight or branched, containing 2 to 20 carbon atoms and 1 to 4 double bonds, a hydrocarbon chain of 2 to 20 carbon atoms, either straight or branched and containing 1 to 4 alcohol or ether oxygen atoms or alkylaryl containing 1 to 4 aromatic rings and 7 to 25 carbon atoms.

$R_1$ is alkyl, straight or branched, of 1 to 20 carbon atoms, alkenyl, straight or branched, containing 2 to 20 carbon atoms and 1 to 4 double bonds, a hydrocarbon chain of 2 to 20 carbon atoms, either straight or branched, and containing 1 to 4 alcohol or ether oxygen atoms or alkylaryl containing 1 to 4 aromatic rings and 7 to 25 carbon atoms;

$R_2$ is alkyl of 1 to 6 carbon atoms or alkoxy alkyl of 1 to 6 carbon atoms; $R_1$ in (v) and (vi) being ortho, meta or para to X or $CH_2X$, respectively.

Representative compounds according to the invention include, as examples:

D-Arg-Arg-Pro-Hyp-Gly-Phe-NH-C(R)-CO-D-Phe-Leu-Arg where R is

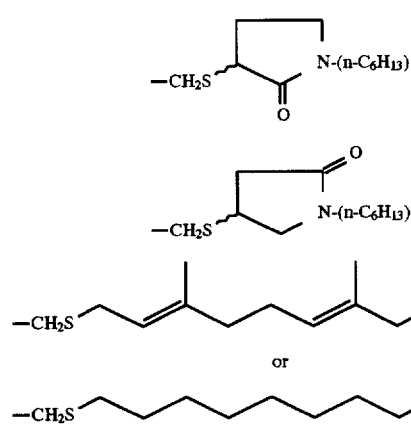

These compounds demonstrate a high degree of potency as bradykinin antagonists. This may be attributed to binding of the hydrophobic "exo" site on the receptor or to capture by a nearby membrane surface.

The hydrophobic extension can serve as a linker to attach other bioactive molecules to the enhanced bradykinin antagonists where $R_1$ or Z is as defined but modified such that a distal hydrogen is replaced by a suitably protected thiol, hydroxyl, amine or carboxylic acid moiety. Suitably protected means any known or commonly employed protecting group compatible with solution or solid-phase synthesis of peptides or oligonucleotides.[22] More specifically, $R_1$ or Z in the case of (iv) or (vii), is an alkyl, alkenyl or alkylaryl hydrocarbon chain containing 2 to 25 atoms and one of the following functional groups in suitably protected form: hydroxyl, thiol, amine (1° or 2°) or carboxylic acid or carboxylic ester. The entire peptide may be fully deprotected or attached to a solid support via the C-terminal carboxylic acid.

The compounds where Z is (i) can be synthesized as follows:

τ-butyrolactam can be N-alkylated with $R_1$ by displacement of suitable leaving group Q, such as bromo, iodo, mesylate, triflate or tosylate in a polar aprotic solvent such as dimethylformamide or dimethylsulfoxide using prior deprotonation of the amide nitrogen using a strong non-nucleophilic base such as sodium hydride. The alkylated lactam 3 can then be activated by introduction of a leaving group "G", alpha to the carbonyl. A variety of methods are known in the art which involve halogen transfer via radicals or halogenation of carbanions formed by alpha proton abstraction by strong bases such as lithium, sodium or potassium alkyl amides in polar aprotic solvents.[23,24] The displacement of the leaving group with sulfur nucleophiles such as the sulfhydryl or sulfide anion derived from suitably protected cysteines or homocysteines or the hydroxyl or alkoxide anion derived from suitable protected serines or homoserines produces the desired novel amino acids, which can then be incorporated at the correct position in the peptide chain by conventional peptide synthesis techniques.[25]

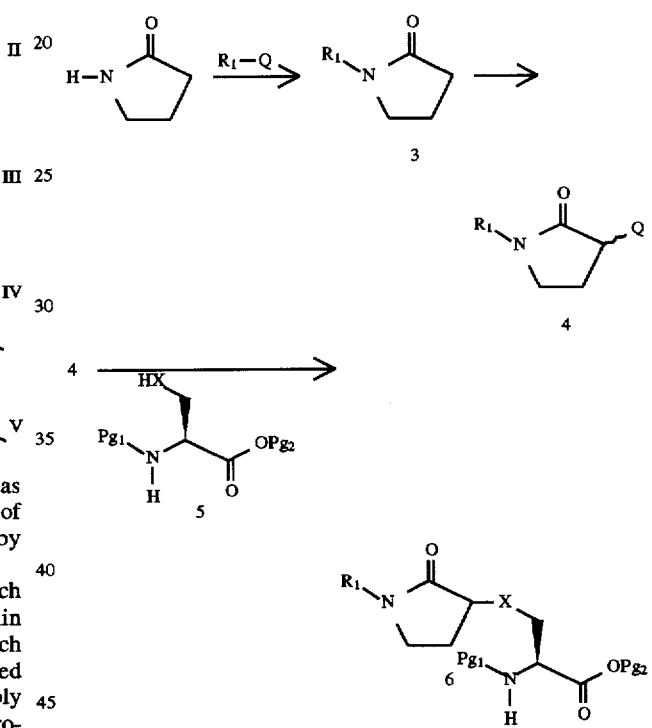

Alternatively, the compounds where Z is (i) can be synthesized by addition of a suitably protected amino acid derivative containing X to a maleimide[18] of structure 7. Borohydride reduction of succinimides 8 may produce hydroxy lactams of structure 9. These hydroxylactams can be reduced to 10 by TFA/triethylsilane reduction. It is possible under borohydride reduction conditions to obtain the unsaturated lactam 11. This olefinic intermediate can be reduced by hydrogenation over excess palladium catalyst to provide lactam 10. These amino acid analogs can be incorporated in the correct position in the peptide chain by methods well known in the literature.[25]

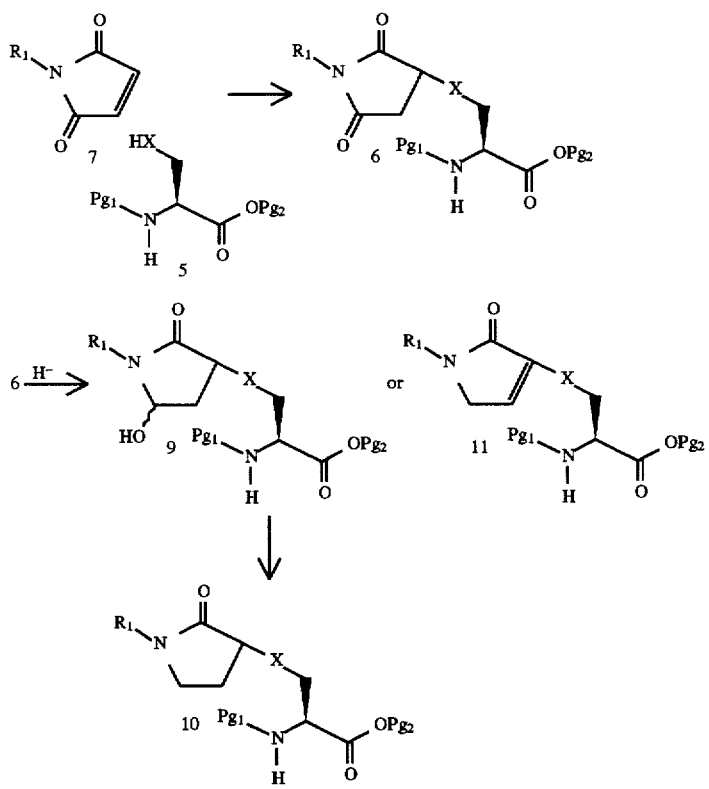

Compounds where Z is (ii) can be formed by the following method:

The enolate anion of lactam 3 can be derivatized with arylselenium halide reagents to produce a 2-arylselenide derivative. Hydrogen peroxide induced selenoxide formation and elimination provides the α-β unsaturated lactam 13. Michael addition of nucleophiles such as the sulfhydryl or sulfide anion derived from suitably protected cysteines or homocysteines or the hydroxyl or alkoxide anion derived from suitable protected serines or homoserines produces the desired novel amino acids 14 which can then be incorporated at the correct position in the peptide chain by conventional peptide synthesis techniques.[25]

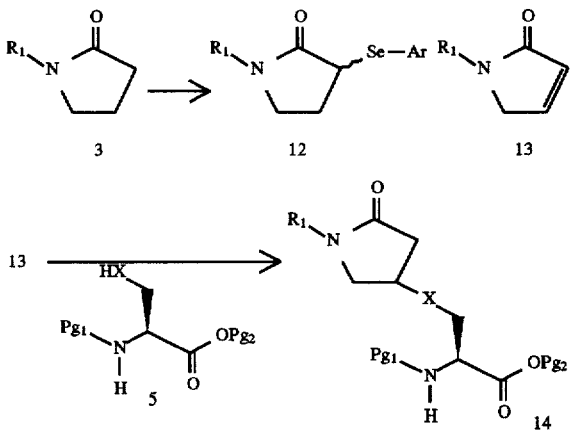

Compounds where Z is (iii) can be synthesized from the corresponding non-prenylated peptide if X contains a sulfhydryl group by alkylation with a prenyl halide in liquid ammonia or in a polar solvent in the presence of a non-nucleophilic base such as N,N-diisopropyl-N-ethylamine or potassium carbonate.

Amino acid residues containing prenyl groups where X contains sulfur or oxygen can be synthesized under similar conditions and then incorporated into the peptide by conventional peptide synthesis techniques which do not require the use of concentrated TFA or HF, such as Fmoc chemistry techniques, employing very acid-sensitive resins.[26]

The compounds where Z is (iv) can be synthesized from primary alkyl iodide compounds of formula $R_1$-I using similar alkylation chemistry. Specifically, such compounds can be synthesized from the corresponding non-alkylated peptide if X contains a sulfhydryl group by alkylation with an alkyl halide derived from $R_1$ in liquid ammonia or in a polar solvent in the presence of a non-nucleophilic base such as N,N-diisopropyl-N-ethylamine or potassium carbonate. Amino acid residues containing $R_1$ groups where X contains sulfur or oxygen can be synthesized using bases such as $K_2CO_3$ and then incorporated into peptide by conventional peptide synthesis techniques. The $K_2CO_3$ method is preferred for serine or homoserine analogs.

Compounds where Z is (v) and where X is sulfur can be synthesized by reaction of suitably substituted thiophenols 15 with a suitably protected beta-lactone 16 derived from serine or by Michael addition to a suitably protected dehydroalanine.

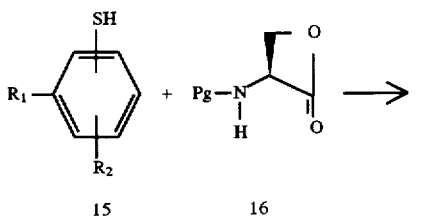

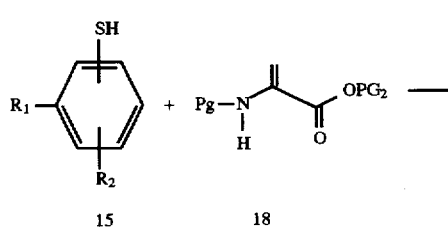

Where X is oxygen, the compound may be synthesized by addition of a suitably functionalized phenol 19, by Michael addition to a suitably protected dehydroalanine.

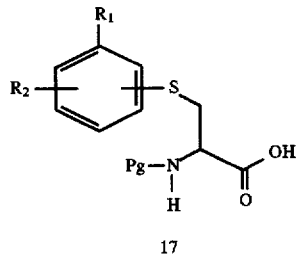

The synthetic amino acid residue can then be incorporated into the peptide by methods well known in the art.[25]

Compounds where Z is (vi) and X is oxygen, $CH_2O$, sulfur or $CH_2S$ can be synthesized as follows:

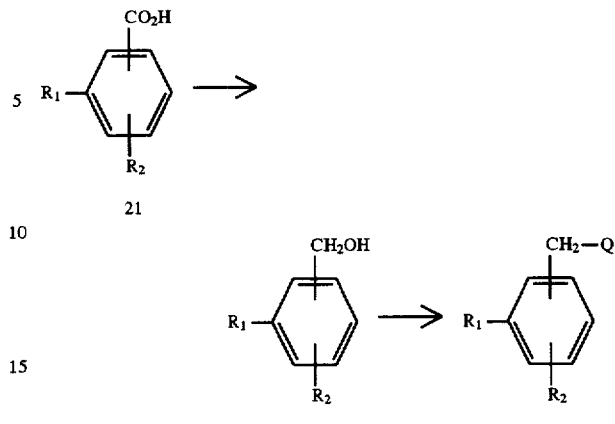

Suitably substituted benzoic acid derivatives 21 can be reduced by strong reducing agents such as lithium aluminum hydride or borane to the corresponding benzyl alcohol derivative 22. Compound 22 can be derivatized with common reagents, such as HBr or sulfonyl chlorides in the presence of tertiary amine or pyridine, to produce 23 where Q is a common leaving group such as chloride, bromide, iodide, mesylate or tosylate, or triflate.

The compounds where Z is (vi) can be synthesized from the corresponding non-alkylated peptide if X contains a sulfhydryl group by alkylation with 23 in liquid ammonia. If X contains sulfur or oxygen, the heteroatom may be alkylated with 23 in a polar solvent in the presence of a non-nucleophilic base such as N,N-diisopropyl-N-ethylamine or potassium carbonate, if the amino acid residue is suitably protected at the amino group. The alkylated homocysteine or homoserine analog may be incorporated into peptide by conventional peptide synthesis techniques. The use of $DMF/K_2CO_3$ is preferred for serine or homoserine analogs.

Compounds where Z is (vii) can be synthesized by conventional peptide synthesis techniques well known in the art, where the residue in question is simply an α-amino acid with a carboxylate side chain such as glutamic, aspartic or α-aminocaproic acid, coupled to an amine of formula $H_2NZ$. Similarly, the amino acid residue can contain a basic side chain such as α-aminopropanoic acid, α-aminobutanoic acid, ornithine, lysine or homolysine coupled to a carboxylic acid of formula $HO_2C$-Z. The coupling may be done on a partially deprotected peptide on a resin support or on a suitably protected amino acid before incorporation into the peptide.

Compounds in which $R_1$ contains functional groups such as thiols, amines, carboxylic acids or hydroxyls in suitably protected forms, can be synthesized as described above for the compounds where Z is (i), (ii), (v) or (vi). Similarly, in the case of compounds where Z is (iv) or (vii), Z is modified such that a distal hydrogen is replaced by a suitably protected thiol, hydroxyl, amine or carboxylic acid moiety and can be synthesized as described above. Suitably protected is defined as any known or commonly employed protecting group compatible with solution or solid-phase synthesis of peptides or oligonucleotides. More specifically, $R_1$, or Z in the case where Z is (iv) or (vii), is an alkyl, alkenyl or alkylaryl hydrocarbon chain containing 2 to 25 carbon atoms and one of the following functional groups in suitably protected form: hydroxyl, thiol, amine (1° or 2°) or carboxylic acid or carboxylic ester. The entire peptide may be fully deprotected or attached to a solid support via the C-terminal carboxylic acid.

Therapeutic application of bradykinin antagonists include traumatic, inflammatory or pathological conditions mediated by bradykinins or their closely related metabolites. These conditions may include treatment of bites, stings, general trauma, head trauma, inflammatory conditions including inflammatory bowel disease, burns, rashes, "shock" or hypotension associated with sepsis, and pain, especially pain associated with burns, or surgical or dental procedures. The compounds of the invention may be administered topically, or by injection or infusion or as an oral suspension in an appropriate vehicle. The dosage and manner of administration will be defined by the application of the bradykinin antagonist and can be determined by routine methods of clinical testing to find the optimum human dose. It is contemplated that doses in the range of 0.01 mg/Kg to 100 mg/Kg of active compound should be used.

The invention is described further by the following examples which represent preferred embodiments of the invention. These examples are intended to be illustrative and instructive and are not intended to be limiting.

EXAMPLE 1

D-Arginyl-L-arginyl-L-prolyl-L-(4R-hydroxy)-prolyl-glycyl-L-phenylalanyl-S-(4-(N-hexyl)-pyrolidinone)-cysteinyl-D-phenylalanyl-L-leucyl-L-arginine

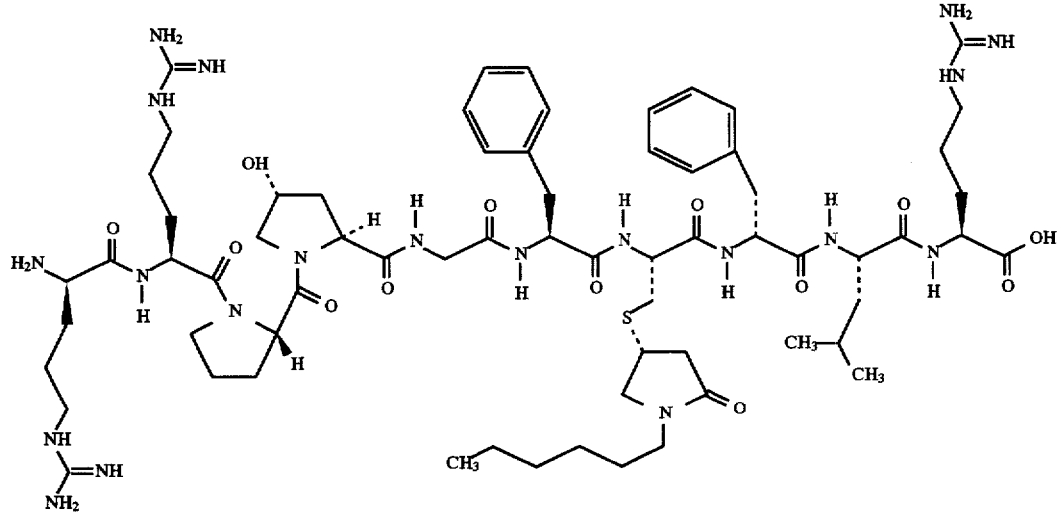

Intermediate A:

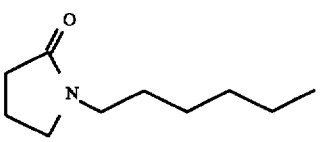

N-(Hexyl)-pyrrolidinone: To a suspension of NaH (470 mg, 11.8 mmol) in 15 mL dry DMF was added pyrrolidinone (1.0 g, 11.8 mmol). The solution was stirred 90 minutes at room temperature. Iodohexane (1.91 mL, 11.8 mmol) was added. The reaction mixture was stirred overnight at which time the mixture was poured onto 15 mL H$_2$O and extracted three times with ether. The combined organic layers were then dried over MgSO$_4$ and evaporated under reduced pressure. Flash chromatography (5% MeOH in CH$_2$Cl$_2$) yield 1.97 g (99.5%) of compound A. $^1$H NMR (CDCl$_3$) δ 3.38 (2H, t, J=7.5 Hz), 3.27 (2H, t, J=7.5 Hz), 2.39 (2H, t, J=7.5 Hz), 2.02 (2H, dt, J=15, 7.5 Hz), 1.50 (2H, m), 1.30 (6H, m), 0.89 (3H, t, J=5.6 Hz).

Intermediate B:

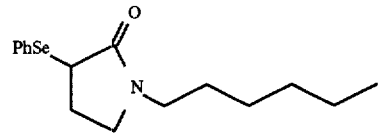

3-(Phenylselenyl)-(N-hexyl)-pyrrolidinone: To diisopropyl amine (1.75 mL, 12.4 mmol) in 20 mL THF at 0° C. was added n-BuLi (4.97, mL, 2.5M, 12.4 mmol) dropwise. The solution was stirred 10 minutes and then cooled to −78° C. Compound A (1 g, 5.92 mmol) was added in 10 mL THF dropwise. The resulting mixture was stirred 1 hour at −78° C. Phenylselenenyl chloride (1.13 g, 5.92 mmol) and HMPA (1.03 mL, 5.92 mmol) in 10 mL THF were added dropwise. The mixture was stirred overnight, allowing to warm to room temperature. The solution was quenched with H$_2$O and extracted three times with EtOAc. The combined organic layers were washed with brine and dried over Na$_2$SO$_4$. Evaporation under reduced pressure was followed by flash chromatography on silica gel (5% MeOH in CH$_2$Cl$_2$) to yield 1.45 g (76%) of the compound B. $^1$H NMR (CDCl$_3$) δ 7.69 (2H, d, J=7.5 Hz), 7.28 (3H, m), 3.93 (1H, dd, J=9.4, 4.5 Hz), 3.20 (2H, t, J=7.5 Hz), 3.09 (2H, t, J=7.5 Hz), 2.53 (1H, dq, J=13.5, 7.5 Hz), 2.15 (1H, dq, J=13.5, 3.75 Hz), 1.43 (2H, m), 1.28 (6H, m), 0.90 (3H, t, J=7.5 Hz).

Intermediate C:

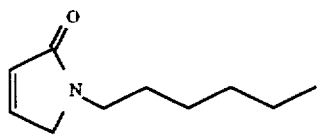

(N-hexyl)-3,4-dehydropyroolidinone: To a solution of compound B (1.3 g, 4.0 mmol) in 20 mL CH$_2$Cl$_2$ at 0° C. was added 30% H$_2$O$_2$ (482 μL, 4.0 mmol). The reaction mixture was stirred for 1 hour at 0° C. and then quenched with saturated ammonium chloride solution. The resulting mixture was extracted three times with $CH_2Cl_2$, evaporated under reduced pressure and dried over $Na_2SO_4$. Flash chromatography (5% MeOH in $CH_2Cl_2$) yielded 460 mg (69%) of the α,β-unsaturated lactam. $^1H$ NMR ($CDCl_3$) δ 7.07 (1H, d, J=6 Hz), 6.20 (1H, d, J=6 Hz), 3.99 (2H, s), 3.44 (2H, t, J=6 Hz), 1.56 (2H, m), 1.31 (6H, m), 0.89 (3H, t, J=7.5 Hz).

Intermediate D:

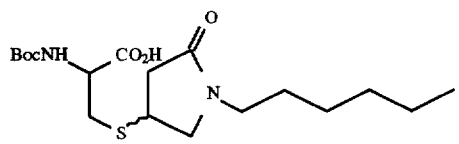

L-(N-tertbutoxycarbonyl)-S-(4-(N-hexyl)-Pyrrolidinone)-cysteine: To a solution of compound C (460 mg, 2.75 mmol) in 21 mL piperidine was added Boc-cysteine (3.04 g, 13.8 mmol). The mixture was degassed with nitrogen and then placed in a 100° C. oil bath. The reaction mixture was refluxed for 2 hours at which time no starting lactam remained. The solution was evaporated under reduced pressure. Flash chromatography (10% MeOH in $CH_2Cl_2$ with 1% AcOH) yielded 378 mg (35%) of the final product. $^1H$ NMR ($CDCl_3$) δ 5.45 (1H, m), 4.57 (1H, m), 3.71 (1H, m), 3.58 (1H, m), 3.29 (3H, m), 3.08 (2H, m), 2.85 (1H, dd, J=17, 7.5 Hz), 2.43 (1H, dd, J=18.7, 7.5 Hz), 1.49 (11H, s), 1.28 (6H, m), 0.89 (3H, t, J=7.5 Hz). Anal. ($C_{18}H_{32}N_2O_5S$)

Compound E: D-Arginyl-L-arginyl-L-prolyl-L-(4R-hydroxy)-prolyl-glycyl-L-phenylalanyl-(S-4-(N-hexyl)-pyrolidinone)-cysteinyl-D-phenylalanyl-L-leucyl-L-arginine Compound D was incorporated into the peptide using an ABI model 430 automated peptide synthesizer (0.25 mmol scale, using HOBt/carbodiimide preactivation and commercially available Boc-(Nw-tosyl)-arginine PAM resin. The peptide was cleaved using hydrogen fluoride containing 10% anisole as a carbonium ion scavenger at 0° for 1 hour. The crude peptide was extracted into 10% acetic acid in water and purified by preparative high pressure liquid chromatography (15–70% acetonitrile in water, 0.1% TFA, over 40 minutes, 100 mL/min. Waters Delta Pak $C_{18}$ column) to provide the desired product as a colorless lyophilate.

Low resolution Laser Desorption Mass Spectrum Calculated M/z=1429 Found 1428.

Amino acid analysis: Gly 1.00 (1); Arg 3.12 (3); Pro 0.97 (1); Leu 0.92 (1); Phe 2.08 (2); Hyp 0.91 (1).

EXAMPLE 2

D-Arginyl-L-arginyl-L-prolyl-L-(4R-hydroxy)-prolyl-glycyl-L-phenylalanyl-(S-farnesyl)-cysteinyl-D-phenylalanyl-L-leucyl-L-arginine

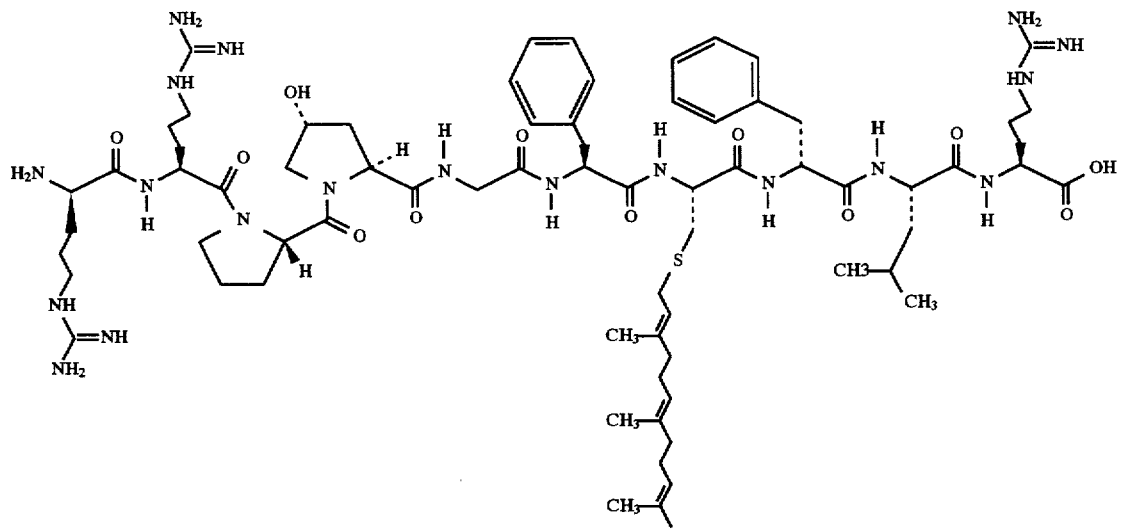

D-Arginyl-L-arginyl-L-prolyl-L-(4R-hydroxy)-prolyl-glycyl-L-phenylalanyl-(S-4-(N-hexyl)-pyrolidinone)-cysteinyl-D-phenylalanyl-L-leucyl-L-arginine[18] (80.0 mg, trifluoroacetate salt) was suspended in 6 mL anhydrous liquid ammonia and was treated with a mixture of 72 uL of farnesyl bromide in 0.6 mL of dry tetrahydrofuran. The reaction was allowed to warm to room temperature and the ammonia boiled off. The residue was taken up in methanol and concentrated in vacuo. The crude product was purified by preparative C18 HPLC (35–80% acetonitrile in water, 0.1% trifluoroacetic acid, over 40 minutes, 10 mL/min. 1" semi-preparative column). The product (35.2 mg) was isolated as a colorless lyophilate.

Low Resolution Laser Desorption Mass Spectrum Calculated M/z=1470 (M+H) Found 1470 (M+H)

Amino acid analysis: Gly 1.02 (1); Arg 2.97 (3); Pro 1.05 (1); Leu 0.95 (1); Phe. 200 (2); Hyp 1.02 (1).

Peptide Sequence Found: Arg-Arg-Pro-Hyp-Gly-Phe-X-Phe-Leu-Arg.

(X=unrecognized amino acid derivative, probably farnesyl cysteine).

EXAMPLE 3

D-L-Arginyl-L-arginyl-L-prolyl-L-(4R-hydroxy)-prolyl-glycyl-L-phenylalanyl-(S-(n-hexyl))-cysteine-D-phenylalanyl-L-leucyl-L-arginine

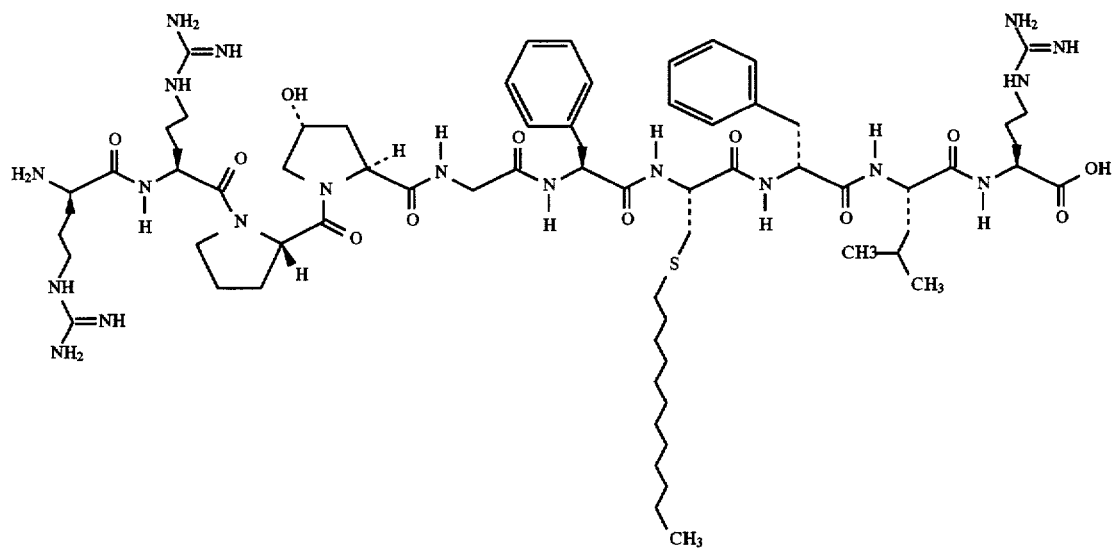

D-Arginyl-L-arginyl-L-prolyl-L-(4R-hydroxy)-prolyl-glycyl-L-phenylalanyl-cysteinyl-D-phenylalanyl-L-leucyl-L-arginine[18] (25 mg. TFA salt) was dissolved in 5 mL of condensed liquid ammonia and treated with a solution of 18

EXAMPLE 4

D-Arginyl-L-arginyl-L-prolyl-L-(4R-hydroxy)-prolyl-glycyl-L-phenylalanyl-(S-(n-hexyl)-benzyl)-cysteine-D-phenylalanyl-L-leucyl-L-arginine

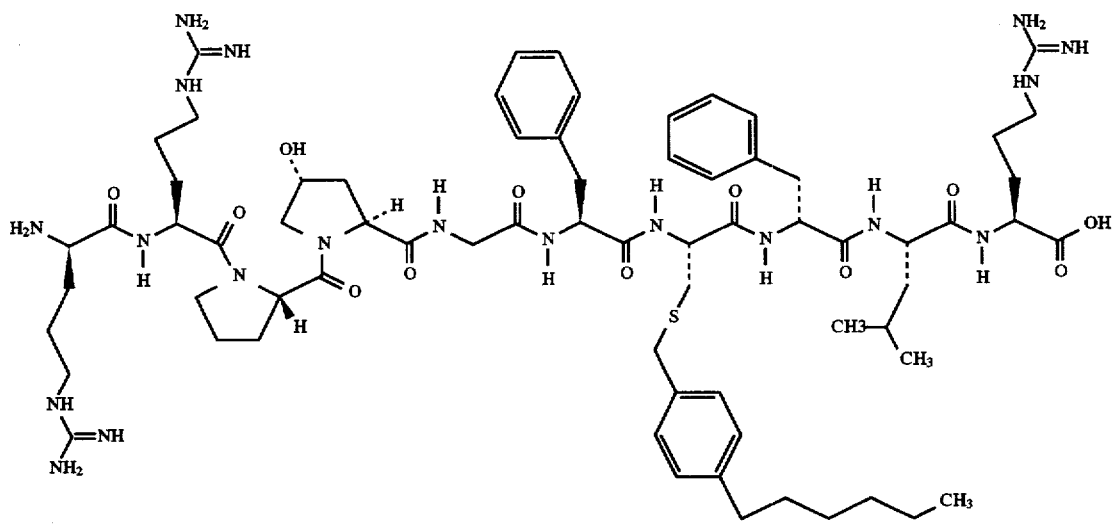

uL of 1-iodododecane in 120 uL of dry THF. The reaction was allowed to stir as the ammonia boiled off through a bubbler over 2 hours. The residue was taken up in methanol and the solvent was removed by rotary evaporation. Small volumes of MeOH (~10 mL) were added and removed in vacuo to remove the majority of residual ammonia. The crude product was purified by preparative reverse phase HPLC on a 1" Vydac $C_{18}$ column using a gradient of 20–28% acetonitrile in water containing 0.1% TFA at a flow rate of 10 mL/min. The purified compound was freeze-dried to produce 5.5 mg of a colorless lyophilate.

Low Resolution Laser Desorption Mass Spectrum Calculated M/z=1432 Found 1432.

Amino acid analysis: Gly 1.02 (1); Arg 2.84 (3); Pro 1.18 (1); Leu 0.97 (1); Phe 1.98 (2); Hyp 1.01 (1).

Intermediate A:

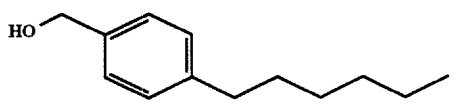

4-(n-hexyl)-benzylalcohol: Lithium aluminum hydride (1.13 g) was suspended in 70 mL of anhydrous ethyl ether under nitrogen, and chilled to 0° C. A solution of 4-(n-hexyl)-benzoic acid (1.75 g) in anhydrous ethyl ether was added dropwise to the reaction mixture over 40 minutes, while cooling was maintained by an ice bath. The reaction was allowed to warm to room temperature and stirring was continued overnight (approximately 15 hours). The reaction was quenched with potassium hydrogen sulfate (42 mmoles) in 120 mL of water. The reaction mixture was extracted three times with ether. The combined organic extracts were washed with 3N hydrochloric acid (3×50 mL), once with saturated sodium bicarbonate, once with water, and finally with saturated sodium chloride solution. The solution was dried over anhydrous magnesium sulfate, filtered and concentrated to 1.60 g of material which was used without further purification.

Intermediate B:

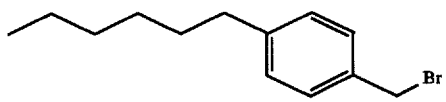

4-(n-Hexyl)-benzylbromide: Compound A (100 mg) was dissolved in 10 mL of chloroform and the resulting solution was saturated with hydrogen bromide gas. The reaction was allowed to stir approximately 15 hours and was then quenched by careful addition of 10 mL of saturated sodium bicarbonate solution. The organic layer was separated and washed with water, saturated sodium chloride solution and dried over magnesium sulfate. The mixture was filtered and the filtrate was concentrated by rotary evaporation to provide 120 mg of compound B.

D-Arginyl-L-arginyl-L-prolyl-L-(4R-hydroxy)-prolyl-glycyl-L-phenylalanyl-S((4-n-hexyl)-benzyl)-cysteine-D-phenylalanyl-L-leucyl-L-arginine: D-Arginyl-L-arginyl-L-phenylalanyl-prolyl-L-(4R-hydroxy)-prolyl-glycyl-L-S-cysteinyl-D-phenylalanyl-L-leucyl-L-arginine[18] (24 mg, TFA salt) and triethylamine (5.85 uL) were dissolved in 1 mL of a 2:1 (v/v) mixture of ethanol and water. Compound B (3.6 mg) was added and the reaction stirred approximately 15 hours at room temperature. The desired compound was purified by $C_{18}$ reverse phase chromatography on a 1" Dynamax semi-preparative column, eluting with a gradient of 20–80% acetonitrile in water containing 0.1% trifluoroacetic acid, at a flow rate of 10 mL/min. The fractions containing pure compound were collected and freeze-dried to produce the desired compound (13 mg) as a colorless lyophilate.

Low Resolution Laser Desorption Mass Spectrum Calculated M/z=1438 Found 1437. (Within experimental error with our instrumentation.)

Amino acid analysis: Gly 1.04 (1); Arg 3.12 (3); Pro 0.98 (1); Leu 0.93 (1); Phe 2.04 (2); Hyp 0.88 (1).

EXAMPLE 5

D-Arginyl-L-arginyl-L-prolyl-L-(4R-hydroxy)-prolyl-glycyl-L-phenylalanyl-(S-(4-n-hexyl)-phenyl)-cysteine-D-phenylalanyl-L-leucyl-L-arginine

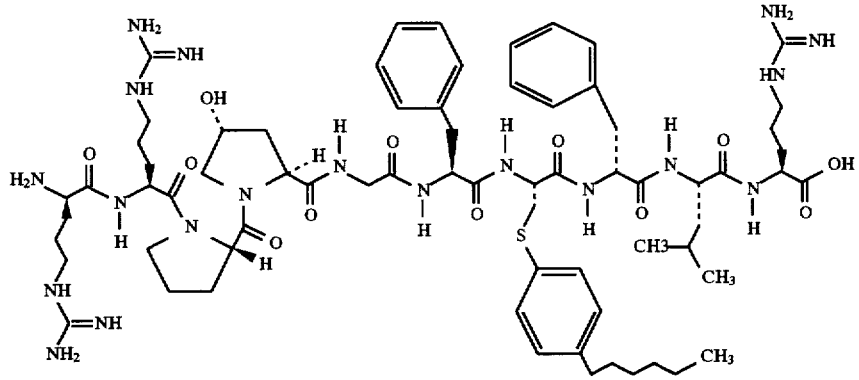

Intermediate A:

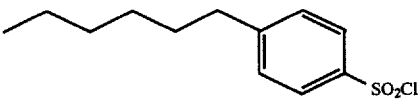

4-(n-Hexyl)-benzenesulfonyl chloride: 1-Phenylhexane (4.72 mL) was heated to 70° C. A mixture of potassium sulfate (0.57 g) in 2.5 mL of chlorosulfonic acid was added dropwise at a rate such that the reaction temperature did not exceed 75° C. An additional portion of 2.5 mL of chlorosulfonic acid was added and the reaction stirred at 70° for approximately 3 hours. The reaction mixture was poured onto ice and the resulting mixture was extracted with chloroform. The organic extracts were washed with 5% sodium carbonate solution, water and finally saturated sodium chloride solution. The solution was carefully dried over magnesium sulfate and concentrated in vacuo. The compound was used in the next step without further purification.

Intermediate B:

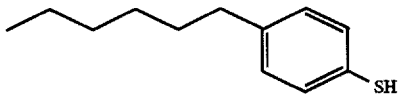

4-(n-Hexyl)-thiophenol: Compound A was chilled to 0° and treated with a mixture of 10 mL sulfuric acid in 62.5 mL of water. After stirring ten minutes, zinc powder (9 g) was added slowly; stirring was continued an additional 45 minutes at 0° C. The reaction was then heated to reflux for 15 hours, then cooled to room temperature and poured into ice in water and extracted with ether. The combined ether layers were washed with water and brine, dried over magnesium sulfate, and concentrated in vacuo to 3.7 g of crude material. Distillation at reduced pressure (<1 torr, 75° C.) provided 2.9 g of B as a colorless liquid.

Intermediate C:

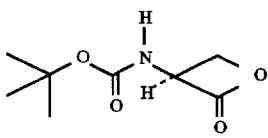

S-3-(N-tert-Butoxycarbony)-amino-2-oxo-oxirane: Triphenyl phosphine (3.85 g) was dissolved in 60 mL of a 9:1 mixture of acetonitrile/tetrahydrofuran and chilled to −55° C. Dimethylazodicarboxylate (1.61 mL) was added to this solution over 10 minutes. After an additional 10 minutes of stirring, N-Boc-L-Serine (3.0 g) in 60 mL of a 9:1 mixture of acetonitrile and tetrahydrofuran was added dropwise over 20 minutes. This mixture was stirred for 30 minutes at −55° C. and then allowed to arm to room temperature. Stirring was continued for 15 hours. The solvent was removed and the compound was purified by flash chromatography on silica gel (30% EtOAc/Hexane) to provide 1.3 g of the desired product.

Intermediate D:

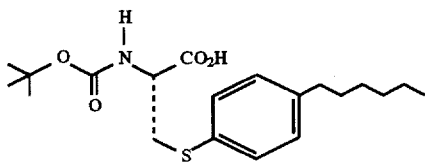

L-(N-tert-Butoxycarbonyl)-(S-(4-n-hexyl)-phenyl)-cysteine: Compound B (1.54 g) was added dropwise to a suspension of 182.4 mg of sodium hydride in 8 mL of dimethylformamide. The solution stirred for an additional 50 minutes and was then canulated into a solution of compound C (1.2 g) in 50 mL of dimethylformamide. The reaction stirred for 2.5 hours and was then quenched with 0.5M phosphoric acid, and the mixture extracted with ethyl acetate. The combined ethyl acetate layers were concentrated in vacuo. The product was purified by flash chromatography (methanol in chloroform) to provide 1.6 g of the desired product as an oil.

Compound E: D-Arginyl-L-arginyl-L-prolyl-L-(4R-hydroxy)-prolyl-glycyl-L-phenylalanyl-(S-(4-n-hexyl)-phenyl)-cysteinyl-D-phenylalanyl-L-leucyl-L-arginine Compound D was incorporated into the peptide using an ABI model 430 automated peptide synthesizer (0.5 mmole scale, using HOBt/carbodiimide preactivation, and commercially available Boc-(N$^w$-tosyl)-arginine PAM resin. The peptide was cleaved using hydrogen fluoride containing 10% anisole as a carbonium ion scavenger at 0° for 1 hour. The crude peptide was extracted into 10% acetic acid in water and purified by preparative high pressure liquid chromatography to provide 200 mg of the desired product as a colorless lyophilate.

Low Resolution Laser Desorption Mass Spectrum Calculated M/z=1424 Found 1424.

Amino acid analysis: Gly 1.11 (1); Arg 3.34* (3); Pro 1.03 (1); Leu 0.93 (1); Phe 1.92 (2); Hyp 0.88 (1).

* Artificially high due to overlap of reference peak.

The following rat uterus antagonist data was obtained by comparing compounds of the invention with compounds (1) and (2) referred to earlier. The standard rat uterus in vitro pA$_2$ measurement was made as follows: Female Sprague-Dawley rats (200–250 g) were pretreated with stilbesterol (100 μg/kg sc) and killed 18 hours later by a blow on the head and exsanguinated. Uterine horns were removed, placed under a 1 g resting tension in 4 mL tissue baths containing De Jalon's solution at 31° C. and aerated with air. Concentration-effect curves were constructed to bradykinin in the absence and presence of antagonist (preincubated for 15 minutes). Antagonist potency was calculated according to the method of Arunlakshana and Schild (Br. J. Pharmacol., 14:48–58, 1959). Following exposure to the highest concentration of antagonist (in each case $10^{-5}$M), each tissue was washed at 10-minute intervals for 40 minutes, after which time a concentration-effect curve was again constructed for bradykinin. The pD$_2$ (-log molar concentration of agonist producing 50% of the original maximum response to bradykinin) for bradykinin at this time was calculated and compared to the pD$_2$ of the initial control concentration-effect curve for bradykinin. The difference in pD$_2$ values compared to concurrent control reflected the percentage recovery of agonist response.

The results obtained are shown in Table 1:

TABLE 1

Rat Uterus Antagonis Data

D — Arg — Arg — Pro — Hyp — Gly — Phe — X — D — Phe — Leu — Arg

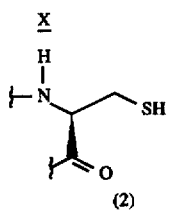

(2)

pA$_2$ = 7.1 ± 0.10 (n = 3) 100% Recovery
No Partial agonism at 10 u M.

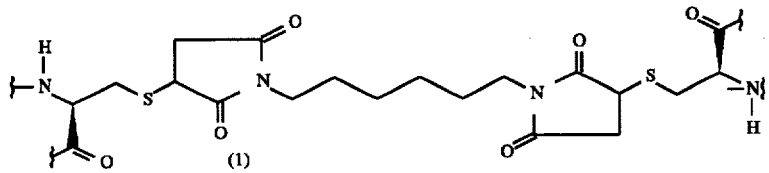

(1)

pA$_2$ = 8.5 ± 0.3 (n = 3) 50% Recovery
No Partial agonism at 10 uM.

TABLE 1-continued

Rat Uterus Antagonis Data
D—Arg—Arg—Pro—Hyp—Gly—Phe—X—D—Phe—Leu—Arg

Example 1.
$pA_2 = 8.7 \pm 0.12$ (n = 7) 75% Recovery
~15% Partial agonism at 10 uM.

Example 2.
$pA_2 = 7.7 \pm 0.10$ (n = 6) 0% Recovery
No Partial agonism at 10 uM.

Example 3.
$pA_2 = 7.3 \pm 0.10$ (n = 9) 0% Recovery
No Partial agonism at 10 uM.

Example 4.
$pA_2 = 8.1 \pm 0.12$ (n = 5) 0% Recovery
No Partial agonism at 10 uM.

Example 5.
$pA_2 = 6.9 \pm 0.10$ (n = n) 21% Recovery
No Partial agonism at 10 uM.

It will be appreciated that various modifications may be made in the invention as described above. Accordingly, the scope of the invention is defined in the following claims wherein:

References identified by number hereinbefore are listed below:

1. Farmer, S. G. and Burch, R. M., The Pharmacology of Bradykinin Receptors, in Bradykinin Antagonists, R. M. Burch, ed., Marcel Dekker, Inc. New York, pp. 1–31, (1991)
2. Griesbacher, T., Lembeck, F., Effect of Bradykinin Antagonists on Bradykinin Induced Plasma Extravasation, Venoconstriction, Prostaglandin E2 Release, and Nociceptor Stimulation and Contraction of the Iris Sphincter Muscle in the Rabbit, Br. J. Pharmacol., 92:333–340 (1987)
3. Taiwo, Y. O. and Levine, J. D., Characterization of the Arachadonic Acid Metabolites Mediating Bradykinin and Noradrenaline Hyperalgesia, Brain Res., 458:402–406 (1988)
4. Steranka, L. R. et al, Bradykinin as a Pain Mediator: Receptors Are Localized to Sensory Neurons, and Antagonists Have Analgesic Actions, Proc. Nat. Acad. Sci. USA, 85:3245–3249 (1988)
5. Dray, A., Bettaney, J., Forster, P. and Perkins, M. N., Bradykinin-Induced Stimulation of Afferent Fibres is Mediated Through Protein Kinase C., Neurosci. Lett., 91:301–307 (1988)
6. Steranka, L. R., Farmer, S. G. and Burch, R. M., Antagonists of B2 Bradykinin Receptors, FASEB J., 32019–2025 (1989)
7. Haley, J. E., Dickenson, A. H. and Schachter, M., Electrophysiological Evidence for a Role of Bradykinin in Chemical Nociception in the Rat, Neurosci. Lett., 97:198–202 (1989)
8. Marceu, F., Lussier, A., Regoli, D., Giroud, J. P., Pharmacology of Kinins: Their Relevance to Tissue Injury and Inflammation, Gen. Pharmacol., 14:209–229 (1983)
9. Proud, D., Kaplan, A. P., Kinin Formation: Mechanism and Role in Inflammatory Disorders, Annu. Rev. Immunol., 6:49–84 (1988)
10. Colman, R. W., Wong, P. Y., Kallikrein-Kinin System in Pathologic Conditions, in Bradykinin, Kallidin and Kallikrein, Handbook of Experimental Pharmacology, Vol. 25, Erdos, E. G. ed., Springer Verlag, New York (1979)
11. Greaves, M. W., Inflammation and Mediators, Br. J. Dermatol., 119:419–426 (1988)
12. Martinez-Brotons, F., Oncins, J. R., Mestres, J., Amargos, V., Reynaldo, C., Plasma kallikrein-kinin system in patients with uncomplicated sepsis and septic shock—comparison with cardiogenic shock., Thrombosis and Haemostasis, 58:709–713 (1987)
13. Farmer, S. G., Airway Pharmacology of Bradykinin and Abraham, William M., Bradykinin Antagonists in a Sheep model of Allergic Asthma, in Bradykinin Antagonists, R. M. Burch, ed., Marcel Dekker, Inc., New York, pp. 213–236 and 261–276 (1991)
14. Unterberg, A., Dautermann, C., Baethemann, A., Muller-Esterl, W., The kallikrein—kinin system as mediator in vasogenic brain edema—Part 3: Inhibition of the kallikrein-kinin system in traumatic brain swelling, *J. Neurosurgery*, 64:269-276 (1986)

15. Holder, I. A., Neely, A. N., Hagerman factor-dependent kinin activation in burns and its theoretical relationship to postburn immunosuppression syndrome and infection, *Journal of Burn Care and Rehabilitation*, 11:496503 (1990)

16. Sicuteri, F., Vasoneuroactive substances and their implication in vascular pain, *Res. Clin. Stud., Headache*, 1:6 (1967)

17. Dray, A. and Perkins, M., Bradykinin and inflammatory pain, *TINS*, 16:99-104 (1993)

18. Cheronis, J. C., Whalley, E. T., Nguyen, K. T., Eubanks, S. R., Allen, L. G., Duggan, M. J., Loy, S. D., Bonham, K. A. and Blodgett, J. K., A New Class of Bradykinin Antagonists: Synthesis and in Vitro Activity in Bissuccinimidoalkane Peptide Dimers, *J. Med. Chem.*, 1563-1572 (1992)

19. Whalley, E. T., Solomon, J. A., Modafferi, D. M., Bonham, K. A., Cheronis, J. C., CP-0127, a novel potent bradykinin antagonist, increases survival in rat and rabbit models of endotoxin shock, *Agents and Actions*, 38:413-420 (1992)

20. Herbette, L. G., Pharmacokinetic and Pharmacodynamic Design of Lipophilic Drugs Based on a Structural Model for Drug Interactions with Biological Membranes, *Pestic. Sci.*, 35:363-368 (1992)

21. Kyle, D. J. and Burch, R. M., A survey of Bradykinin Receptors and Their Antagonists, *Curr. Opin. Ivest. Drugs*, 2:5-20 (1993). Stewart, J. M. and Vavrek, R. J., Chemistry of Peptide B2 Bradykinin Antagonists, in *Bradykinin Antagonists*, R. M. Burch, ed., Marcel Dekker, Inc., New York. pp. 51-96 (1991)

22. See, for example, Greene, T. W. and Wuts, P. G. M., Protective Groups in Organic Synthesis, John Wiley and Sons, Inc., New York (1991)

23. *Chemistry Letters*, 1509 (1984)

24. *Tet. Lett.*, 28:2477 (1987), *J. Org. Chem.*, 43:3687 (1978)

25. See detailed procedures in reference 18; for general information, see Baarany, G., Kneib-Cordonier, N. and Mullen, D. G., Solid-Phase Peptide Synthesis, A Silver Anniversary Report, *Int. J. Peptide Protein Res.*, 30:705-739 (1987)

What is claimed is:

1. A compound comprising a bradykinin antagonist peptide and a hydrophobic side chain; linked through the amino acid residue in the 0, 1, 2, 3, 5 or 6 position of said side chain comprising

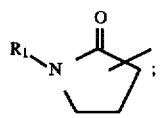

(ii) a prenyl group;

(iii)($C_1$–$C_{20}$) alkyl optionally comprising 1 to 4 double bonds, or 1 to 4 alcohol or ether oxygen atoms;

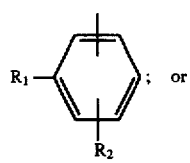

-continued

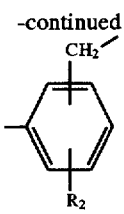

where $R_1$ is ($C_1$–$C_{20}$)alkyl optionally comprising 1 to 4 double bonds, or 1 to 4 alcohol or ether oxygen atoms; and $R_2$ is ($C_1$–$C_6$)alkyl or ($C_1$–$C_6$)alkoxyalkyl;

said compound having bradykinin antagonist activity.

2. A compound of claim 1 wherein said side chain is attached at the 6-position of the bradykinin antagonist peptide.

3. A compound of claim 2 having the following structure:

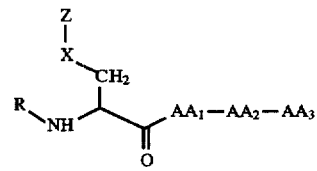

wherein:

X is S or $CH_2$;

$AA_1$ is D-phenylalanine, D-Tic, D-(2-indanyl)-glycine, D-(cyclopentyl)glycine, D-hydroxyproline, or proline;

$AA_2$ is L-Oic, L-cyclopentylglycine, leucine, phenylalanine, or proline;

$AA_3$ is L-arginine;

R is D-Arg-Arg-Pro-Hyp-Gly-$AA_4$- or D-Arg-Arg-Pro-Pro-Gly-$AA_4$-, where $AA_4$ is L-thienylalanine or L-phenylalanine; and Z is (i), (ii), (iii) or (iv).

4. A compound according to claim 3 wherein X is sulfur and $R^1$ is an alkyl of 2-20 carbon atoms.

5. A compound according to claim 3 wherein R is D-Arg-Arg-Pro-Hyp-Gly-Phe-.

6. A compound according to claims 3, 4 or 5 wherein Z is (i).

7. A compound according to claims 3, 4 or 5 wherein Z is (ii).

8. A compound according to claims 3, 4 or 5 wherein Z is (iii).

9. A compound according to claims 3, 4 or 5 wherein Z is (iv).

10. A compound according to claims 3, 4 or 5 wherein Z is (v).

11. A compound according to claim 1 which is D-Arginyl-L-arginyl-L-prolyl-L-(4R-hydroxy)-prolyl-glycyl-L-phenylalanyl-L-(S-N(hexyl)-pyrolidinone)-cysteinyl-D-phenylalanyl-L-leucyl-arginine.

12. A compound according to claim 1 which is D-Arginyl-L-arginyl-L-prolyl-L-(4R-hydroxy)-prolyl-glycyl-L-phenylalanyl-L-(S-(farnesyl)-cysteinyl-D-phenylalanyl-L-leucyl-arginine.

13. A compound according to claim 1 which is D-Arginyl-L-arginyl-L-prolyl-L-(4R-hydroxy)-prolyl-glycyl-L-phenylalanyl-L-(S-(n-hexyl))-cysteine-D-phenylalanyl-L-leucyl-arginine.

14. A compound according to claim 1 which is D-Arginyl-L-arginyl-L-prolyl-L-(4R-hydroxy)-prolyl-glycyl-L-phenylalanyl-L-(S-(n-hexyl)-benzyl)-cysteine-D-phenylalanyl-L-leucyl-arginine.

15. A compound according to claim 1 which is D-Arginyl-L-arginyl-L-prolyl-L-(4R-hydroxy)-prolyl-glycyl-L-phenylalanyl-L-(S-(n-hexyl)-phenyl)-cysteine-D-phenylalanyl-leucyl-arginine.

16. A compound according to claims 1, 4, 5, 11, 12, 13, 14 or 15 in the form of a pharmaceutically acceptable salt.

17. A pharmaceutical composition comprising an effective amount of a compound according to claims 1, 2, 3, 4, 5, 11, 12, 13, 14 or 15, and a pharmaceutically acceptable carrier therefor.

18. In a method of treating inflammation using a bradykinin antagonist peptide, the improvement comprising using a bradykinin antagonist peptide according to claim 1.

19. A pharmaceutical composition comprising a bradykinin antagonist of claim 1 and a pharmaceutically acceptable carrier.

20. A method of treating head trauma comprising administering to a patient in need of such treatment, an amount of a bradykinin antagonist of claim 1 effective to reduce cerebral edema associated with said head trauma.

21. A method of alleviating pain comprising administering to a patient in need of such treatment, an amount of a bradykinin antagonist of claim 1 effective to reduce said pain.

22. A method of claim 21 wherein said pain is associated with migraine.

23. A method of claim 22 wherein said pain is associated with surgical procedures or cancer.

24. A method of treating asthma comprising administering to a patient in need of such treatment, an amount of a bradykinin antagonist of claim 1 effective to inhibit bronchoconstriction associated with said asthma.

* * * * *